United States Patent [19]
Taniguchi et al.

[11] Patent Number: 6,054,620
[45] Date of Patent: Apr. 25, 2000

[54] PROCESS FOR PRODUCING A TERTIARY AMINE HAVING HIGH QUALITY

[75] Inventors: Hideki Taniguchi; Yasuyuki Mimura; Hiroshi Abe, all of Wakayama, Japan

[73] Assignee: Kao Corporation, Tokyo, Japan

[21] Appl. No.: 09/161,485

[22] Filed: Sep. 28, 1998

[30] Foreign Application Priority Data

Oct. 7, 1997 [JP] Japan ................................. 9-274320

[51] Int. Cl.$^7$ ................................................ C07C 209/00
[52] U.S. Cl. ................................ 564/497; 564/2; 564/500
[58] Field of Search ................................ 564/2, 497, 500

[56] References Cited

U.S. PATENT DOCUMENTS

| | | | |
|---|---|---|---|
| 3,169,995 | 2/1965 | Roy | 260/585 |
| 3,337,630 | 8/1967 | Moke | 260/583 |

FOREIGN PATENT DOCUMENTS

| | | | |
|---|---|---|---|
| 0 500 038 | 8/1992 | European Pat. Off. | |
| 1 768 743 | 11/1971 | Germany | |
| 4-266858 | 9/1992 | Japan | |

*Primary Examiner*—Samuel Barts
*Attorney, Agent, or Firm*—Oblon, Spivak, McClelland, Maier & Neustadt, P.C.

[57] ABSTRACT

The present invention provides a process for producing a tertiary aliphatic amine having high quality having little non-amines such as esters and alcohols, which is less colored, and which can be converted into a derivative without turbidity.

That is, the present invention provides the process which comprises the steps of adding at least one alkali substance of potassium hydroxide and sodium hydroxide or an aqueous solution thereof to the crude tertiary amine product mixture and distilling the mixture to obtain the tertiary amine having a high quality.

In addition, the tertiary amine has the formula: $R_1R_2N\text{—}R_3$, wherein $R_1$ and $R_2$ being a saturated or unsaturated hydrocarbon having 6 to 28 carbon atoms, $R_3$ being a saturated or unsaturated hydrocarbon having 1 to 5 carbon atoms.

13 Claims, No Drawings

PROCESS FOR PRODUCING A TERTIARY AMINE HAVING HIGH QUALITY

BACKGROUND OF THE INVENTION

1. Field of the Invention

The present invention relates to a process for producing a tertiary amine having high quality and the having little non-amines such as esters and alcohols, which is less colored, and which can be converted into a derivative without turbidity.

2. Description of the Background

An aliphatic tertiary amine prepared from tallow, coconut oil, palm oil and the like is an important intermediate for household and industrial products, used in many applications that include a softener for clothes, an antistatic agent, a gasoline additive, a shampoo, a conditioner, a microbicide and a detergent.

As a process for producing an aliphatic tertiary amine, a process for producing it from a fat through an aliphatic acid and a process for producing it from a fat through an aliphatic higher alcohol are known. However, the aliphatic tertiary amine produced by these processes has problems that it is much colored in the conversion into derivatives and that it becomes turbid in a long-term storage to give products poor in appearance.

DE-A 1 768 743 discloses adding an alkali to an amine product, being primary, secondary or tertiary, having a molecular weight of 80 or larger, and distilling the mixture to remove esters and non-reacted aliphatic alcohols.

However DE-A 1 768 743 merely discloses broadly that amine is treated by alkali, it doesn't disclose that the amine which is represented by following formula (I) is treated by NaOH or KOH in order to remove ester or unreacted aliphatic alcohol;

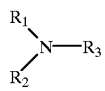

(I)

wherein $R_1$ and $R_2$ being a saturated or unsaturated hydrocarbon having 6 to 28 carbon atoms, $R_3$ being a saturated or unsaturated hydrocarbon having 1 to 5 carbon atoms.

JP-A 4-266 858, corresponding to EP-A 500038, discloses that a crude aliphatic tertiary amine product is contacted with an adsorbent in the presence of an inorganic alkali, but the added alkali has been removed out through an adsorbent before the subsequent step of distillation.

However, when an aliphatic tertiary amine is produced from a fat through an aliphatic higher alcohol in particular, the process has problems that such impure non-amines as esters (wax), alcohols, and the like contaminate the aliphatic tertiary amine, that the impure non-amines cannot be eliminate completely, and that derivatives made from the aliphatic tertiary amine become turbid in a long-term storage to give products poor in appearance.

SUMMARY OF THE INVENTION

The present invention to solve the problems provides a process for producing an aliphatic tertiary amine from a fat through an aliphatic higher alcohol, wherein the aliphatic tertiary amine contains little non-amines such as esters and alcohols, is less colored, and is converted into derivatives to give high quality without turbidity in a long-term storage.

DETAILED DESCRIPTION OF THE PREFERRED EMBODIMENTS

The present invention provides a process for producing a tertiary amine having high quality, which comprises adding a mixture containing a crude aliphatic tertiary amine represented by the formula (I) to a sodium hydroxide and/or potassium hydroxide, and distilling the mixture to obtain the tertiary amine having a high quality;

(I)

wherein $R_1$ and $R_2$ being a saturated or unsaturated hydrocarbon having 6 to 28 carbon atoms, $R_3$ being a saturated or unsaturated hydrocarbon having 1 to 5 carbon atoms.

The present invention more preferably provides the process as claimed in the above-mentioned process, in which $R_1$ and $R_2$ have 8 to 22 carbon atoms and $R_3$ is methyl.

The present invention preferably provides the process as claimed in the above-mentioned process, in which the tertiary amine product mixture has been obtainable by reacting two molecules of an aliphatic primary alcohol with one molecule of methylamine.

The present invention preferably provides the process as claimed in the above-mentioned process, in which 0.05 to 5 percent by weight of the alkali substance is added per the tertiary amine of the product mixture.

The present invention more preferably provides the process as claimed in the above-mentioned process, in which the alkali substance is potassium hydroxide.

The present invention preferably provides the process as claimed in the above-mentioned process, in which esters, waxes and the unreacted alcohol are removed out from the tertiary amine product mixture.

The preferred embodiment for carrying out the present invention will now be described in detail.

Firstly, a mole-ratio (a/b) of the aliphatic primary alcohol (a) to the methyl amine (b) is in the range of about 2.0 to 10.0. That is, the methyl amine of 1.0 to 5.0 equivalent is corresponded to the aliphatic primary alcohol when the tertiary amine is prepared. The catalyst used in the preparation of the tertiary amine is what mainly consists of Cu or Ni. Examples of the catalyst include Cu—Ni, Cu—Zn, Cu—Co, and catalysts prepared by adding at least one selected from the group consisting of Pd, Pt, Ru, and Rh among Group VIII platinum metals to thereof. The amount of the catalyst to be used is 0.1 to 5% by weight based on the aliphatic primary alcohol. The reaction temperature is generally in the range of 150 to 230° C. and the pressure is from atmospheric pressure to 10 MPa (gauge pressure).

Namely, two molecules of an aliphatic primary alcohol is reacted with one molecule of methylamine to produce an aliphatic tertiary amine.

The aliphatic primary alcohol used in the present invention a saturated or unsaturated aliphatic primary alcohol having 6 to 28 carbon atoms, preferably 8 to 22 carbon atoms. An example of the above-mentioned reaction is represented by the following formula:

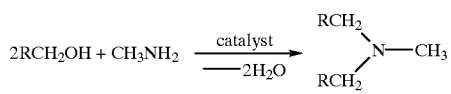

wherein R being a saturated or unsaturated hydrocarbon having 5 to 27 carbon atoms.

The aliphatic tertiary amine obtained by the present invention contains a tertiary amine having 13 to 61 carbon atoms, preferred 17 to 49 carbon atoms in total. As examples of the tertiary amine, N-methyldidodecylamine, N-methyldioctadecylamine, N-dodecyl-N-methyl-octadecylamine and the like are cited.

In the present invention, a following conduction is a distillation of an amine represented by formula (I) after addition of sodium hydroxide and/or potassium hydroxide.

Among them, potassium hydroxide is preferred. A form of the alkali added into the amine is variable and any of the group consisting of powder, aqueous solution, flake, and the like.

In the present invention, an amount of an alkali is preferably 0.05 to 5%, more preferably 0.3 to 2%, by weight as compared with the aliphatic tertiary amine in the resultant mixture.

After adding the alkali, the resultant product is heated at a temperature of 150 to 250° C. for 0 to 5 hours, preferably 1 to 3 hours, under the atmospheric pressure, and is distilled under a pressure of 0.1 to 50 Torr (corresponding to about 0.05 to 7 kPa), preferably under a pressure of 1 to 20 Torr, which is less than an atmospheric pressure, at a temperature of 150 to 250° C. for 3 to 10 hours, preferably 5 to 8 hours.

An aliphatic tertiary amine produced by the process in the present invention has little non-amines such as esters (wax) and unreacted alcohols because of removal of non-volatile amines and amides, and is less colored, and has so high quality as to be converted into a derivative without turbidity, when the derivative is in a long-term storage. That is, the present invention can provide the aliphatic tertiary amine having high quality.

EXAMPLES

Now, unless otherwise stated, the percentages in the following examples are given by weight.

Examples 1 to 3

600 g of dodecyl alcohol (a product of Kao Corporation; Kalcohl 20) and 3 g (corresponding to 0.5% by weight based on the alcohol used as the raw material) of a copper-nickel catalyst were fed into all four-necked flask. The system was purged with nitrogen while stirring and the temperature of the system was initiated to heat. When the temperature of the system reached at 100° C., hydrogen gas was blown into the system at a flow rate of 40 l/hr with a flowmeter and the temperature of the system was raised to a reaction temperature, i.e., 200° C. At this temperature, the introduction of methylamine gas was initiated and a reaction was conducted for 7 hours. After the completion of the reaction, the reaction resultant was filtered to remove the catalyst, thereby providing crude N-methyldidodecylamine.

200 g of the crude N-methyldidodecylamine was put in a 500 ml Hertz-flask. Using the other flask, a potassium hydroxide was weighed to be 0.2%, 0.5%, or 1.0% as compared with the crude N-methyldidodecylamine and dissolved by 1 g of deionized water. The solution of the sodium hydroxide was put into the above-mentioned Hertz-flask. After setting on apparatus for a distillation (capillary distillation), a mixture in the Hertz-flask was conducted by bubbling with nitrogen gas under an atmospheric pressure at a temperature of 200° C. for 2 hours. And then, the pressure in the Hertz-flask was reduced to 5 to 10 Torr, and the mixture in the Hertz-flask was heated at a temperature of 250° C. Further the mixture was distilled and separated at the temperature for 5 hours to obtain N-methyldidodecylamine.

An acid value and an amount of non-amines (such as esters and alcohols) contained in the amine were measured, and observed a turbid of the derivative thereof by the following manner 1. Table 1 shows the results.

Now, an amount of non-amines was measured by a resin-adsorption method. Namely, a mixture, provided by that 2 g of the obtained amine was dissolved into 50 ml of isopropylalcohol, was conducted by an adsorption into 30 ml of a cationic ion-exchange resin. To weigh an amount of a residue which was not adsorbed into the ion-exchange resin and which was in isopropylalcohol, the isopropylalcohol is substituted for hexane finally and dried. Further, a percentage of the residue by weight was measured as compared with the amine, therefor the percentage of non-amines was calculated.

Comparative Example 1

An N-metyldidodecylamine was obtained by the same manner as Example 1 except that a potassium hydroxide was not used. An acid value and an amount of non-amines thereof were measured to observe a turbid the derivative thereof by the same manner as Example 1. Table 1 shows the results.

Comparative Example 2

After a crude N-methyldidodecylamine was obtained by the same manner as Example 1 to 3, each 0.5% of a 48% solution of sodium hydroxide, an active carbon, and Kyoward 600S (a product of Kyowa Chemical Industry Co.) as compared with the amine were added to the crude amine. The resultant mixture was agitated at a temperature of 90° C. for 2 hours under an atmosphere of nitrogen. After the active carbon and Kyoward600S was filtered, an N-methyldidodecylamine was separated and obtained by a distillation.

An acid value and an amount of non-amines (esters and alcohols) contained in the amine were measured and observed a turbid of the derivative thereof by the same manner as Example 1. Table 1 shows the results.

TABLE 1

| | An amount of an added potassium hydroxide | an acid value | esters (%) | alcohols (%) | a turbid of a derivative (30° C./3 months) |
|---|---|---|---|---|---|
| Comparative example 1 | none | 0.9 | 0.9 | 0.3 | turbid |
| Example 1 | 0.2 | 0.2 | 0.1 | <0.1 | clear |
| Example 2 | 0.5 | 0.1 | <0.1 | <0.1 | clear |
| Example 3 | 1.0 | <0.1 | <0.1 | <0.1 | clear |
| Comparative example 2 | — | 0.1 | 0.9 | 0.3 | turbid |

Example 4

An N-methyldidodecylamine was obtained by the same manner as Example 1 except that a sodium hydroxide was substituted for a potassium hydroxide and the sodium hydroxide was weighed to be 1.0% as compared with the crude N-methyldidodecylamine. An acid value and an amount of non-amines thereof were measured, and observed a turbid of the derivative thereof by the same manner as Example 1. Table 2 shows the results.

Comparative Example 3

An N-methyldidodecylamine was obtained by the same manner as Example 1 except that a calcium hydroxide was substituted for a potassium hydroxide and the calcium hydroxide was weighed to be 1.0% as compared with the crude N-methyldidodecylamine. An acid value and an amount of non-amines thereof were measured, and observed a turbid of the derivative thereof by the same manner as Example 1. Table 2 shows the results.

TABLE 2

| | a kind of an added alkali | an acid value | esters (%) | alcohols (%) | a turbid of a derivative (30° C./3 months) |
|---|---|---|---|---|---|
| Example 4 | NaOH | <0.1 | <0.1 | 0.1 | clear |
| Comparative example 3 | Ca(OH)$_2$ | <0.1 | 0.4 | 0.3 | clear |

We claim:

1. A process for producing a tertiary amine having the formula:

$$R_1R_2N\text{—}R_3$$

wherein $R_1$ and $R_2$ are each independently saturated or unsaturated hydrocarbon having 6 to 28 carbon atoms, and $R_3$ is saturated or unsaturated hydrocarbon having 1 to 5 carbon atoms; which process consists essentially of adding at least one alkali substance selected from the group consisting of potassium hydroxide and sodium hydroxide, to a crude tertiary amine product mixture obtained from the reaction of an aliphatic alcohol with a mono-alkyl amine; and distilling the mixture to obtain a tertiary amine, whereby said distilled tertiary amine product mixture comprises a reduced content of esters, waxes and unreached alcohol.

2. The process of claim 1, wherein $R_1$ and $R_2$ each independently have 8 to 22 carbon atoms, and $R_3$ is methyl.

3. The process of claim 1, wherein the tertiary amine product mixture is obtained by reacting an aliphatic primary alcohol (a) with methylamine (b) in a mole ratio (a/b) of about 2.0 to 10.0.

4. The process of claim 1, wherein 0.05 to 5% by weight of the alkali substance is added based upon the tertiary amine of the product mixture.

5. The process of claim 1, wherein the alkali substance is potassium hydroxide.

6. The process of claim 3, wherein said reaction is conducted in the presence of a catalyst comprising Cu or Ni.

7. The process of claim 6, wherein the amount of catalyst used is 0.1 to 5% by weight based on the aliphatic primary alcohol.

8. The process of claim 3, wherein said reaction is conducted at a temperature of about 150 to 230° C.

9. The process of claim 1, wherein said aliphatic tertiary amine is selected form the group consisting of N-methyldidoceylamine, N-methyldioctadecylamine and N-dodecyl-N-methyl-octadecylamine.

10. The process of claim 1, wherein said aliphatic tertiary amine contains no more than 0.1% of alcohol therein.

11. The process of claim 1, wherein said aliphatic tertiary amine contains no more than 0.1% of ester therein.

12. The process of claim 1, wherein said aliphatic tertiary amine has an acid value of no more than 0.2.

13. A process for producing a tertiary amine having the formula:

$$R_1R_2N\text{—}R_3$$

wherein $R_1$ and $R_2$ are each independently saturated or unsaturated hydrocarbon having 6 to 28 carbon atoms, and $R_3$ is saturated or unsaturated hydrocarbon having 1 to 5 carbon atoms; which process consists essentially of adding at least one alkali substance selected from the group consisting of potassium hydroxide and sodium hydroxide, to a crude tertiary amine product mixture obtained from the reaction of an aliphatic alcohol with a mono-alkyl amine; and distilling the mixture to obtain a tertiary amine, whereby esters, waxes and unreacted alcohol are removed out from the tertiary amine product mixture.

* * * * *